(12) United States Patent
Malkowsky et al.

(10) Patent No.: US 8,617,376 B2
(45) Date of Patent: Dec. 31, 2013

(54) PROCESS FOR THE ELECTROCHEMICAL PREPARATION OF GAMMA-HYDROXYCARBOXYLIC ESTERS AND GAMMA-LACTONES

(75) Inventors: Itamar Michael Malkowsky, Speyer (DE); Florian Stecker, Mannheim (DE); Simone Lutter, Ludwigshafen (DE); Olivier Abillard, Mannheim (DE); Ralf Pelzer, Fuerstenberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/594,028

(22) Filed: Aug. 24, 2012

(65) Prior Publication Data

US 2013/0053582 A1 Feb. 28, 2013

Related U.S. Application Data

(60) Provisional application No. 61/526,722, filed on Aug. 24, 2011.

(30) Foreign Application Priority Data

Aug. 24, 2011 (EP) .................................. 11178688

(51) Int. Cl.
*C25B 3/00* (2006.01)
*C25B 3/02* (2006.01)

(52) U.S. Cl.
USPC .......................................... 205/441; 205/427

(58) Field of Classification Search
USPC ................................................ 205/441, 427
See application file for complete search history.

(56) References Cited

U.S. PATENT DOCUMENTS 4,414,079 A * 11/1983 Yamataka et al. ............ 205/352

FOREIGN PATENT DOCUMENTS

| DE | 10 2004 011 427 A1 | 9/2005 |
| EP | 0 635 587 A1 | 1/1995 |
| JP | 57-108274 | 7/1982 |

OTHER PUBLICATIONS

European Search Report issued on Jan. 20, 2012 in corresponding European Application No. 11 17 8688 filed on Aug. 24, 2011 (with an English Translation of Categories).
Tatsuya Shono et al., "Electroreductive Hydrocoupling of Activated Olefins with Ketones or Aldehydes in the Presence of Trimethylchlorosilane", Tetrahedron Letters, vol. 21, 1980, pp. 5029-5032.
Ullmann's Encyclopedia of Industrial Chemistry, 2009 electronic release, VCH-Verlag Weinheim, Volume Electrochemistry, Chapter 3, Electrochemical Cells, pp. 1-2 and 19-24 and Chapter 5, Organic Electrochemistry, Subchapter 5.4.3. Electrochemical Cells, pp. 83-88.
Katrin Bürger, "Reduktive Kupplung von Carbonylverbindungen und heteroanalogen Carbonylverbindungen zu 1,2-Diolen, 1,2-Diaminen und γ-Lactonen an der Graphit-Kathode", Thesis 2003, Universität Münster.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

γ-Hydroxycarboxylic esters and γ-lactones which are suitable as flavors can be prepared by electrochemical reductive cross-coupling of α,β-unsaturated esters with carbonyl compounds in an undivided electrolysis cell having a cathode composed of lead, lead alloys, cadmium, cadmium alloys, mercury, steel, glassy carbon or boron-doped diamonds and a basic aqueous electrolyte comprising an electrolyte salt which suppresses the cathodic formation of hydrogen.

13 Claims, No Drawings

PROCESS FOR THE ELECTROCHEMICAL PREPARATION OF GAMMA-HYDROXYCARBOXYLIC ESTERS AND GAMMA-LACTONES

The present application incorporates by reference the provisional U.S. application 61/526,722 filed on Aug. 24, 2011.

The invention relates to a process for the electrochemical preparation of γ-hydroxycarboxylic esters and γ-lactones by reductive cross-coupling of α,β-unsaturated esters with carbonyl compounds in an undivided electrolysis cell, in which a cathode composed of lead, lead alloys, cadmium, cadmium alloys, mercury, steel, glassy carbon or boron-doped diamonds and a basic aqueous electrolyte comprising an electrolyte salt selected from among bisquaternary and multiquaternary ammonium and phosphonium salts are used.

The invention further relates to the γ-butyrolactone derivatives of the formula I

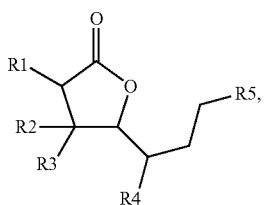

which can be prepared by the process of the invention, and also their use as flavors.

The invention also relates to the γ-hydroxycarboxylic acids or γ-hydroxycarboxylic esters of the formula

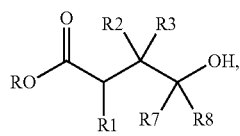

which can likewise be prepared by the process of the invention.

The industrially most important γ-lactone is γ-butyrolactone. It is prepared industrially either by dehydrocyclization of 1,4-butanediol in the gas phase or by hydrogenation of maleic anhydride. A further classical method for preparing γ-lactones is the alkaline hydrolysis of γ-halocarboxylic acids.

The above-described methods always go out from an existing disubstituted $C_4$ framework, so that substitution patterns on the ring cannot be realized convergently. However, methods in which the future lactone ring is built up only by means of C,C-bond coupling are also known. These include, for example, the oxidative coupling of acetic acid with olefins ($C_2+C_2$) or the tert-butyl hydroperoxide-aided cyclization of acrylic acid with alcohols ($C_3+C_1$). In these cases, the substitution of the ring can be controlled by clever use of the appropriate starting materials in the cyclization.

This type of lactone synthesis also includes the reductive coupling (dihydrodimerization) of acrylic esters and carbonyl compounds according to the following reaction scheme:

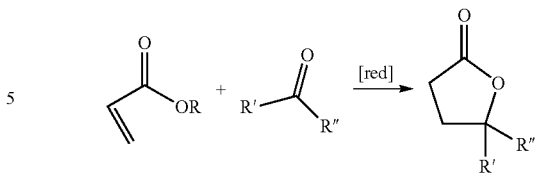

The reductive coupling of acrylic acid derivatives with carbonyl compounds can be effected by means of reducing agents such as magnesium or samarium(II) iodide. Electrochemical methods which avoid the stoichiometric use of a chemical reducing agent have also been described. Fundamental metal studies in this field were carried out in a divided electrochemical cell at a mercury pool cathode in a sulfuric acid electrolyte at cathodic current densities of up to 2.8 $A/dm^2$. In the studies, the reductive coupling of acrylonitrile with acetone was observed, which thus do not yet lead to the lactones.

Proceeding herefrom, Shono et al. (Tetrahedron Lett. 1980, 21, 5029-5032) have described the reductive coupling of α,β-unsaturated esters with aldehydes or ketones in a divided electrochemical cell. The electrolyte used was based on N,N-dimethylformamide (DMF) with N,N,N,N-tetraethylammonium toluenesulfonate ($Et_4NOTs$) as electrolyte salt. Furthermore, stoichiometric amounts of a chlorosilane (trimethylsilyl chloride, TMSCl) were added to activate the carbonyl component. The electrolysis was carried out at a current density of 0.4 $A/dm^2$, which is far removed from industrially relevant current densities of >1 $A/dm^2$. Nobuya et al. (JP 57108274 A) have undertaken a further step toward industrial implementation by using a water-based electrolyte. The preparation of the lactones was carried out in a divided electrolysis cell at current densities of 10 $A/dm^2$. Here, an acidic anolyte (e.g. 10% strength $H_2SO_4$) and a $KH_2PO_4$-buffered catholyte were used. In divided cells, the two electrode spaces are separated by a membrane. Undivided cells are cheaper and industrially easier to realize. Particularly in the case of organic processes, rapid aging of the membrane and therefore unsatisfactory operating lives can be expected.

U.S. Pat. No. 4,414,079 describes the reaction of α,β-unsaturated esters with aldehydes in an undivided cell using, for example, tetra-n-butylammonium sulfate as electrolyte salt. In a further approach, Burger (Katrin Burger, Thesis 2003, Universitat Munster) has carried out the reaction of α,β-unsaturated esters with aldehydes or ketones in an undivided cell. Electrolytes used were binary mixtures of alcohols (e.g. methanol or ethanol) with water or dioxane and also high concentrations of electrolyte salts (e.g. tetrabutylammonium tetrafluoroborate, $Bu_4NBF_4$). Interestingly, graphite electrodes were used in the system described and, owing to their comparatively high hydrogen overvoltage, these could serve as alternatives for lead, mercury and cadmium electrodes. However, the yields of lactone which can be obtained by this process are unsatisfactory since the corresponding homocoupling products and the reduced carbonyl component (i.e. the corresponding alcohol) are formed to a large extent as by-products, even though the homo-coupling of the α,β-unsaturated esters is countered by a high excess of carbonyl compound. In addition, this process is based on the use of electrolytes based on binary organic solvents (alcohol with water or alcohol with dioxane), which makes a complicated separation of the product from the solvent necessary after the electrolysis. The use of alcohol-comprising solvents is also disadvantageous because the alcohol is oxidized (to aldehyde and further) in the electrolysis. As a result, expensive solvent is lost and the aldehyde formed has to be separated off in a complicated manner.

It is therefore an object of the invention to provide a process for the electrochemical preparation of the γ-lactones and γ-hydroxycarboxylic esters by cross-coupling of α,β-unsaturated esters with carbonyl compounds, in which the disadvantages of the prior art, in particular the use of divided electrochemical cells, of low current densities (<1 A/dm$^2$) and the occurrence of yield-reducing secondary reactions are avoided. This object is achieved by the claimed embodiments described below.

The present invention accordingly provides a process for the electrochemical preparation of γ-hydroxycarboxylic esters and/or γ-lactones by reductive cross-coupling of α,β-unsaturated esters with carbonyl compounds in an undivided electrolysis cell, wherein the cathode material is selected from the group consisting of lead, lead alloys, cadmium, cadmium alloys, mercury, steel, glassy carbon and boron-doped diamonds and a basic, aqueous electrolyte comprising at least one electrolyte salt selected from among bisquaternary and multiquaternary ammonium and phosphonium salts is used.

For the purposes of the present invention, a carbonyl compound is an aldehyde or a ketone, preferably an aldehyde. The carbonyl compounds according to the invention preferably have a low solubility in water of less than 100 g/l, more preferably less than 50 g/l, particularly preferably less than 30 g/l, in each case at 20° C. Alkyl and/or aryl groups, which can also comprise further functional groups (for example alcohol, ether, carbonyl, carboxylic acid groups, etc.) and can be alkyl, alkylene or arylene groups interrupted by oxygen, sulfur or nitrogen, are preferably bound to the carbonyl group of the carbonyl compounds. Particular preference is given to aliphatic carbonyl compounds which do not have any further heteroatoms in addition to the carbonyl group. Suitable carbonyl compounds are, for example, pentanal, 2-methylpentanal, hexanal, 2-ethylhexanal, heptanal, 4-formyltetrahydropyran, 4-methoxybenzaldehyde, 4-tert-butylbenzaldehyde, 4-methylbenzaldehyde, glyoxal, glutaraldehyde, methylglyoxal, cyclohexenone, cyclohexanone, diethyl ketone. Particularly preferred carbonyl compounds are pentanal, 2-methylpentanal, hexanal and heptanal.

For the purposes of the present invention, an α,β-unsaturated ester is an acrylic ester derivative which can be substituted independently in positions 2 and 3, with two substituents also being possible in position 3. The substituents are preferably alkyl groups, halogen atoms, C1-C20-alkoxy groups, alkyl, alkylene or arylene radicals interrupted by oxygen, sulfur or nitrogen, nitrile groups and nitro groups. The substituents are preferably selected from the group consisting of methyl, ethyl, n-propyl, isopropyl, n-butyl, tert-butyl, trifluoromethyl, fluorine, chlorine, bromine, iodine, methoxy, ethoxy, methylene, ethylene, propylene, isopropylene, benzylidene, nitrile and nitro. Particular preference is given to substituents selected from the group consisting of methyl, ethyl, methoxy, ethoxy. The α,β-unsaturated ester is preferably a C1-C12-alkyl ester, particularly preferably a C1-C5-alkyl ester, very particularly preferably a methyl or ethyl ester. The α,β-unsaturated esters used according to the invention preferably have a low solubility in water of less than 100 g/l, preferably less than 50 g/l, particularly preferably less than 20 g/l, in each case at 20° C.

α,β-Unsaturated esters and carbonyl compounds are the starting materials for the reductive coupling according to the invention.

An aqueous electrolyte for the purposes of the present invention comprises the starting materials together with water, at least one electrolyte salt and at least one buffer as components. In addition, the electrolyte preferably also comprises at least one complexing agent and/or at least one anode corrosion inhibitor as further components. The aqueous electrolyte in its totality with all components including the starting materials will hereinafter also be referred to as reaction electrolyte. The aqueous composition corresponding to the reaction electrolyte without starting materials will hereinafter also be referred to as supporting electrolyte. The aqueous reaction electrolyte has a water content of preferably at least 20% by weight, particularly preferably at least 50% by weight, in particular at least 75% by weight, based on the total aqueous reaction electrolyte.

The reaction electrolyte according to the invention comprises at least one electrolyte salt, selected from among bisquaternary and multiquaternary ammonium and phosphonium salts, which suppresses the cathodic formation of hydrogen. Preferably, apart from these bisquaternary and multiquaternary ammonium and phosphonium salts, no further electrolyte salts are used. In general, the electrolyte salt is used in an amount in the range from 0.01 to 2.5% by weight, preferably from 0.01 to 1.5% by weight, preferably from 0.01 to 0.5% by weight, particularly preferably from 0.05 to 0.25% by weight, based on the total aqueous reaction electrolyte. Particularly suitable electrolyte salts are bisquaternary ammonium and phosphonium salts (EP 635587 A). Particular preference is given to using bis(dibutylethyl)hexamethylenediammonium hydroxide as electrolyte salt for the electrolyte. Possible counterions are, for example, sulfate, hydrogensulfate, alkylsulfates, arylsulfates, alkylsulfonates, arylsulfonates, halides, phosphates, carbonates, alkyiphosphates, alkylcarbonates, nitrate, alkoxides, hydroxide, tetrafluoroborate or perchlorate. The acids derived from the abovementioned anions are also possible as electrolyte salts, i.e. for example sulfuric acid, sulfonic acids and carboxylic acids. Ionic liquids are also suitable as electrolyte salts. Suitable ionic liquids are described in "Ionic Liquids in Synthesis", edited by Peter Wasserscheid, Tom Welton, Verlag Wiley VCH, 2003, chapters 1 to 3, and also in DE 102004011427 A.

The reaction electrolyte further comprises at least one buffer having a buffering range at a pH of from 7 to 11, preferably from 8 to 10, for buffering the protons formed in the anodic formation of oxygen. Suitable buffers are, for example, hydrogenphosphate or hydrogencarbonate, preferably in the form of their sodium salts. Particular preference is given to using disodium hydrogenphosphate as buffer for the electrolyte. In general, the buffer is used in an amount in the range from 0.9 to 8% by weight, preferably from 4 to 7% by weight, based on the total aqueous reaction electrolyte.

Furthermore, the reaction electrolyte preferably comprises one or more anode corrosion inhibitors such as the borates known for this purpose, preferably disodium diborate and orthoboric acid, in an amount of from 0.4 to 3% by weight, preferably from 1 to 2% by weight, based on the total aqueous reaction electrolyte.

Furthermore, the reaction electrolyte preferably comprises one or more complexing agents in order to prevent the precipitation of iron and lead ions. Mention may be made by way of example of ethylenediaminetetraacetate (EDTA), triethanolamine (TEA), triethylamine, nitrilotriacetate, preferably EDTA in an amount in the range from 0 to 1% by weight, preferably from 0.1 to 0.5% by weight, based on the total aqueous reaction electrolyte, and/or TEA in an amount in the range from 0 to 0.5% by weight, preferably from 0.05 to 0.2% by weight, based on the total aqueous reaction electrolyte.

Instead of TEA, it is possible to use triethylamine in an amount of from 0 to 0.5% by weight, preferably from 0.05 to 0.2% by weight, based on the total aqueous reaction electrolyte.

As anode material, it is possible to use known anode materials; in the case of undivided cells, materials having a low oxygen overvoltage, for example carbon steel, glassy carbon, steel, mercury, cadmium, platinum, iron, nickel, magnetite, lead, lead alloys or lead dioxide, are usually used. Preference is given to using an anode composed of steel, iron, lead or a lead alloy.

As cathodes, use is made of lead, lead alloys, cadmium, cadmium alloys, mercury, steel, glassy carbon or boron-doped diamond electrodes. Preference is given to using lead, lead alloys, cadmium, steel and glassy carbon as cathode materials. Particular preference is given to using lead and lead alloys as cathode materials.

In the aqueous reaction electrolyte according to the invention, the organic starting materials (α,β-unsaturated esters and carbonyl compounds) and the products formed (γ-hydroxycarboxylic esters and γ-lactones) are present as organic phase of an emulsion. The emulsion is maintained during the electrolysis by mechanical agitation such as stirring or pump circulation of the electrolyte in the electrolysis cell, or else by addition of suitable emulsifiers which stabilize the emulsion. The emulsion is preferably maintained during the electrolysis by mechanical agitation such as stirring or pump circulation of the electrolyte. After the electrolysis, demixing of the emulsion can be achieved, for example by stopping the agitation or by addition of a suitable flocculent. After demixing of the emulsion to get an aqueous phase and an organic phase, the products and any unreacted starting materials can easily be separated off with the organic phase from the aqueous electrolyte. This simplifies the separation of the products from the electrolyte.

In the electrolysis of the invention, the starting materials α,β-unsaturated esters and carbonyl compounds are preferably used in an essentially equimolar ratio. The molar ratio of α,β-unsaturated ester used to carbonyl compound used is usually in the range from 0.25 to 4, preferably from 0.5 to 2, particularly preferably from 0.8 to 1.2. While an excess of carbonyl compound is used in the previously known processes for reductive coupling of α,β-unsaturated esters with carbonyl compounds in order to suppress the homo-coupling of the ester, the process of the invention displays a high selectivity to the cross-coupling product of α,β-unsaturated ester and carbonyl compound. When the starting materials are used in an essentially equimolar ratio, particularly good yields of the cross-coupling product can be achieved by means of the process of the invention. The α,β-unsaturated ester is preferably used in an amount of from 1 to 25% by weight, particularly preferably from 5 to 10% by weight, based on the total aqueous reaction electrolyte.

The electrolysis is usually carried out at a current density of at least 1 A/dm$^2$, preferably from 1 to 4 A/dm$^2$. However, it is also possible to carry out the electrolysis at a higher current density of up to 20 A/dm$^2$.

The electrolysis of the invention is usually carried out at a temperature of from 20 to 60° C. and under atmospheric pressure.

The electrolysis can be carried out either continuously or batchwise and in all conventional undivided electrolysis cells, for example in glass beaker cells or plate cells and frame cells or cells having fixed-bed or moving-bed electrodes. Both monopolar and bipolar connection of the electrodes can be employed. The electrolyte in the electrolysis cell is preferably circulated by pumping or stirred, as a result of which its presence as emulsion can be maintained. Very particularly suitable cells are capillary cells or plate stack cells connected in a bipolar manner, in which the electrodes are configured as plates and are arranged parallel to one another (Ullmann's Encyclopedia of Industrial Chemistry, 2009 electronic release, VCH-Verlag Weinheim, Volume Electrochemistry, Chapter 3, Electrochemical Cells and Chapter 5, Organic Electrochemistry, Subchapter 5.4.3. Electrochemical Cells).

In an undivided electrolysis cell, anode space and cathode space are not separated from one another by a membrane. Such undivided cells are cheaper and technically easier to release. Particularly in the case of organic processes, the use of divided cells can lead to rapid aging of the membrane, which results in unsatisfactory operating lives.

In the process of the invention for the electrochemical reductive cross coupling of α,β-unsaturated esters with carbonyl compounds, the γ-lactone or the corresponding γ-hydroxycarboxylic ester can in each case be formed either alone or as a mixture. If necessary, any γ-hydroxycarboxylic ester formed can be converted into the γ-lactone by transesterification after the electrochemical reductive cross-coupling. The transesterification to form the γ-lactone can, for example, be carried out by heating the γ-hydroxycarboxylic ester in the presence of acid. If necessary, the alcohol liberated can be removed from the reaction mixture in order to shift the reaction in the direction of the γ-lactone. Conversely, any γ-lactone formed can be converted into the γ-hydroxycarboxylic ester by transesterification (alcoholysis), for example by heating the γ-lactone in alkaline, nonaqueous alcoholic solutions, after the electrochemical reductive cross-coupling. The γ-hydroxycarboxylic ester can subsequently be converted further into the free acid or the carboxylic acid salt by hydrolysis. For this purpose, the γ-hydroxycarboxylic ester is, for example, heated with aqueous alkaline solutions. As an alternative, the free γ-hydroxycarboxylic acid or its salt can also be prepared directly from the γ-lactone by hydrolysis. This can be carried out, for example, by heating the γ-lactone in aqueous, alkaline solutions.

The invention further provides the γ-butyrolactone derivatives of the general formula I

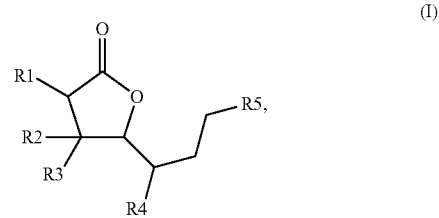

(I)

where
R1, R2 and R3 are each, independently of one another, a hydrogen or an alkyl group having from 1 to 5 carbon atoms, preferably a hydrogen, a methyl or ethyl group, and R4 and R5 are alkyl groups having from 1 to 4 carbon atoms, preferably from 1 to 3 carbon atoms, with R4 and R5 being identical radicals,
which can be prepared by the process of the invention.

The compounds of the formula I can be prepared by the electrochemical cross-coupling according to the invention of α,β-unsaturated esters of the formula II

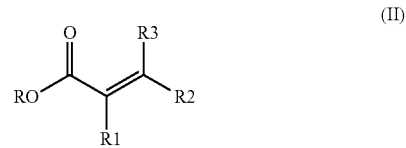

(II)

with 2-alkylalkanals of the formula III

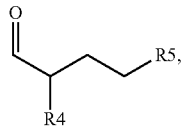
(III)

where R1 to R5 have the same meanings as in the compounds of the formula I and R is an alkyl group, usually an alkyl group having from 1 to 12 carbon atoms, preferably from 1 to 5 carbon atoms, very particularly preferably a methyl or ethyl group.

The invention preferably provides the v-butyrolactone derivatives of the general formula IV

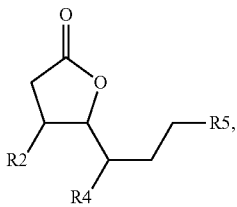
(IV)

where
R2 is a hydrogen or an alkyl group having from 1 to 5 carbon atoms, preferably a hydrogen, a methyl group or an ethyl group, and R4 and R5 are alkyl groups having from 1 to 4 carbon atoms, preferably from 1 to 3 carbon atoms, with R4 and R5 being identical radicals, which can be prepared by the process of the invention.

The compounds of the formula IV can be prepared by the electrochemical cross-coupling according to the invention of α,β-unsaturated esters of the formula II (where R1 and R3 are in each case hydrogen) with 2-alkylalkanals of the formula III.

The 2-alkylalkanals of the formula III can be prepared, for example, by aldol condensation of alkanals having from 3 to 6 carbon atoms (propanal, butanal, pentanal or hexanal).

Particular preference is given to the v-butyrolactone derivatives 4-(2-pentyl)butyrolactone

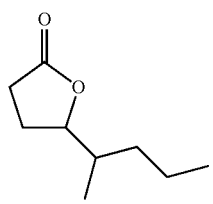
(V)

and 3-methyl-4-(2-pentyl)butyrolactone

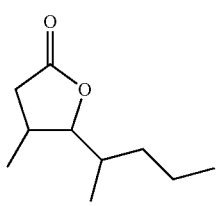
(VI)

which can be prepared by the electrochemical cross-coupling according to the invention of acrylic esters or crotonic esters with 2-methylpentanal.

The invention further provides the γ-hydroxycarboxylic acids and γ-hydroxycarboxylic esters of the general formula VIII

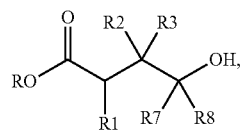
(VII)

where
R1, R2, R3 and R7 are each, independently of one another, a hydrogen or an alkyl group having from 1 to 5 carbon atoms, preferably a hydrogen, a methyl group or an ethyl group, R is a hydrogen or an alkyl group, usually a hydrogen or an alkyl group having from 1 to 5 carbon atoms, and R8 is a branched alkyl group having from 3 to 10 carbon atoms, which can be prepared by the process of the invention.

The invention preferably provides the γ-hydroxycarboxylic acids and γ-hydroxycarboxylic esters of the general formula VIII, where R1, R2 and R3 are each, independently of one another, a hydrogen or an alkyl group having from 1 to 5 carbon atoms, preferably a hydrogen, a methyl group or an ethyl group, R is a hydrogen or an alkyl group, usually a hydrogen or an alkyl group having from 1 to 5 carbon atoms, R7 is a hydrogen and R8 is a branched alkyl group having from 3 to 10 carbon atoms, which can be prepared by the process of the invention.

The compounds of the formula VIII can be prepared by the electrochemical cross-coupling according to the invention of α,β-unsaturated esters of the formula II with the carbonyl compound of the formula VIII

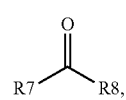
(VIII)

where R7 and R8 have the same meanings as in the compounds of the formula VIII.

Alkyl groups for the purposes of the invention can in principle be either branched or unbranched, either linear or cyclic and either saturated or unsaturated (including multiply unsaturated). They preferably have from 1 to 20, particularly preferably from 1 to 6, carbon atoms. They preferably do not have any heteroatoms.

Aryl groups for the purposes of the invention are aromatic radicals having preferably from 5 to 20 carbon atoms.

The invention further provides for the use of the γ-butyrolactone derivatives of the formula I according to the invention, preferably the γ-butyrolactone derivatives of the formula IV, particularly preferably 4-(2-pentyl)butyrolactone or 3-methyl-4-(2-pentyl)butyrolactone as fragrances or flavors. 4-(2-Pentyl)butyrolactone has a pear-like aroma and 3-methyl-4-(2-pentyl)butyrolactone has a wood-like aroma.

EXAMPLES

The invention will now be illustrated by the following, nonlimiting examples.

Example 1

Electrochemical Preparation of ethyl γ-hydroxypelargonate and 4-pentylbutyrolactone by Reductive Cross-Coupling of Ethyl Acrylate with Hexanal Using an Excess of Hexanal Ethyl acrylate (1.7% by weight) and hexanal (29.7% by weight) were emulsified in an aqueous electrolyte (0.16% by weight of bis(dibutylethyl)hexamethylenediammonium hydroxide (bisquat), 0.38% by weight of EDTA, 0.14% by weight of TEA, 1.45% by weight of $Na_2B_4O_7$ and 5.84% by weight of $Na_2HPO_4$ in water at a pH of 10) (all % by weight are based on the total aqueous reaction electrolyte) and subjected to galvanostatic electrolysis at a current density of 2.23 $A/dm^2$ and a temperature of 20° C. in a pot cell. The current throughput was 2 F/mol of ester. A steel anode and a lead cathode were used as electrodes (electrode area of 0.1 $dm^2$ and spacing of 1 cm). To monitor the reaction, the methyltributylammonium methylsulfate extract (MTBE extract) of a sample of the electrolysis output was analyzed by gas chromatography. A yield of 0.1% of 4-pentylbutyrolactone and a yield of 2.9% of the corresponding ethyl γ-hydroxypelargonate were achieved. This corresponded to a total yield of target products 3.0% of the theoretical yield.

Example 2

Electrochemical Preparation of ethyl γ-hydroxypelargonate and 4-pentylbutyrolactone by Reductive Cross-Coupling of Ethyl Acrylate with Hexanal Using the Starting Materials in an Equimolar Ratio Ethyl acrylate (5.9% by weight) and hexanal (6.0% by weight) were reacted (all % by weight are based on the total aqueous reaction electrolyte) and analyzed as described in example 1. A yield of 4-pentylbutyrolactone of 23.7% and a yield of the corresponding ethyl γ-hydroxypelargonate of 48.0% were achieved. This corresponded to a total yield of target products of 71.7% of the theoretical yield.

Comparative Example 1

Electrochemical Preparation of ethyl γ-hydroxypelargonate and 4-pentylbutyrolactone by Reductive Cross-Coupling of Ethyl Acrylate with Hexanal Using an Excess of Hexanal Corresponding to the reductive coupling described by Burger, ethyl acrylate (1.7% by weight) and hexanal (29.7% by weight) were dissolved in an electrolyte (17.0% by weight of tetrabutylamine tetrafluoroborate ($Bu_4NBF_4$) in a 3:1 mixture of dioxane and ethanol) (all % by weight are based on the total aqueous reaction electrolyte) and subjected to galvanostatic electrolysis at a current density of initially 2.23 $A/dm^2$ and a temperature of 21° C. in a pot electrolysis cell. The current throughput was 2 F/mol of ester. During the course of the electrolysis, the current density dropped to 0.73 $A/dm^2$. A platinum anode and a graphite cathode were used as electrodes (electrode area of 0.1 $dm^2$ and spacing of 1 cm). To monitor the reaction, the methyltributylammonium methylsulfate extract of a sample of the electrolysis output was analyzed by gas chromatography. A yield of 4-pentylbutyrolactone of 2.0% and a yield of the corresponding ethyl γ-hydroxypelargonate of 0.2% were achieved. This corresponded to a total yield of target product of 2.2% of the theoretical yield.

Comparative Example 2

Electrochemical Preparation of ethyl γ-hydroxypelargonate and 4-pentylbutyrolactone by Reductive Cross-Coupling of Ethyl Acrylate with Hexanal Using the Starting Materials in an Equimolar Ratio Ethyl acrylate (5.9% by weight) and hexanal (6.0% by weight) were reacted at 22° C. (all % by weight are based on the total aqueous reaction electrolyte) and subsequently analyzed as described in comparative example 1, with the current density remaining constant during the experiment. A yield of 4-pentylbutyrolactone of 16.5% and a yield of the corresponding ethyl γ-hydroxypelargonate of 0.7% were achieved. This corresponded to a total yield of target products of 17.2% of the theoretical yield.

Example 3

Preparation of Whiskey Lactone

Ethyl crotonate (6.9% by weight) and pentanal (5.2% by weight) were emulsified in an aqueous electrolyte (0.16% by weight of bis(dibutylethyl)hexamethylenediammonium hydroxide (bisquat), 0.38% by weight of EDTA, 0.14% by weight of TEA, 1.45% by weight of $Na_2B_4O_7$ and 5.84% by weight of $Na_2HPO_4$ in water at a pH of 10) (all % by weight based on the total aqueous reaction electrolyte) and subjected to galvanostatic electrolysis at a current density of 2.23 $A/dm^2$ and a temperature of 25° C. in a frame electrolysis cell. The current throughput was 2 F/mol of ester. A steel anode and a lead cathode were used as electrodes (electrode area of 0.1 $dm^2$ and spacing of 1 cm). To monitor the reaction, the MTBE extract of a sample of the electrolysis output is analyzed by gas chromatography. A yield of 3-methyl-4-butyl-butyrolactone (whiskey lactone) of 68.5% and a yield of the corresponding ethyl γ-hydroxycarboxylate of 24.2% were achieved. This corresponded to a total yield of target products of 92.7% of the theoretical yield.

Example 4

Preparation of 4-(2-pentyl)butyrolactone

Ethyl acrylate (5.9% by weight) and 2-methylpentanal (6.0% by weight) were reacted electrochemically using a method analogous to example 3 (all % by weight are based on the total aqueous reaction electrolyte). A yield of 4-(2-pentyl)butyrolactone of 88.4% was achieved.

Example 5

Preparation of 3-methyl-4-(2-pentyl)butyrolactone

Ethyl crotonate (6.7% by weight) and 2-methylpentanal (5.9% by weight) were reacted electrochemically by a method analogous to example 3 (all % by weight are based on the total aqueous reaction electrolyte). A yield of 4-(2-pentyl) butyrolactone of 66.7% and a yield of the corresponding ethyl γ-hydroxycarboxylate of 26.6% were achieved. This corresponded to a total yield of target products of 93.2% of the theoretical yield.

Example 6

Preparation of 3,3-dimethyl-4-pentylbutyrolactone

Methyl 3,3-dimethylacrylate (4.9% by weight) and hexanal (4.3% by weight) were reacted electrochemically by a method analogous to example 3 (all % by weight are based on the total aqueous reaction electrolyte). A yield of 3,3-dimethyl-4-pentylbutyrolactone of 37.2% was achieved.

Example 7

Preparation of 2-methyl-4-butylbutyrolactone

Ethyl methacrylate (6.7% by weight) and pentanal (5.2% by weight) were reacted electrochemically using a method analogous to example 3 (all % by weight are based on the total aqueous reaction electrolyte). A yield of 2-methyl-4-butylbutyrolactone of 81.0% was achieved.

Example 8

Preparation of 2-methyl-4-(2-pentyl)butyrolactone

Ethyl methacrylate (6.7% by weight) and methylpentanal (5.9% by weight) were reacted electrochemically using a method analogous to example 3 (all % by weight are based on the total aqueous reaction electrolyte). A yield of 2-methyl-4-(2-pentyl)butyrolactone of 70.9% was achieved.

The invention claimed is:

1. A process for the electrochemical preparation of γ-hydroxycarboxylic esters, γ-lactones, or both, the process comprising reductive cross-coupling of α,β-unsaturated esters with carbonyl compounds in an undivided electrolysis cell,
   wherein the electrolysis cell comprises a cathode material and a basic, aqueous electrolyte,
   the cathode material is selected from the group consisting of lead, lead alloy, cadmium, cadmium alloy, mercury, steel, glassy carbon, and boron-doped diamond, and the electrolyte comprises at least one electrolyte salt selected from the group consisting of bisquaternary ammonium, multiquaternary ammonium, and phosphonium salt.

2. The process according to claim 1, wherein the α,β-unsaturated esters and carbonyl compounds and a product of the reductive cross-coupling are present as an emulsion in the aqueous electrolyte.

3. The process according to claim 1, wherein the electrolyte salt is a bisquaternary ammonium or phosphonium salt.

4. The process according to claim 1, wherein the cathode material is selected from the group consisting of lead, lead alloy, cadmium, steel and glassy carbon.

5. The process according to claim 1, wherein the electrolysis cell comprises an anode material selected from the group consisting of carbon steel, glassy carbon, steel, mercury, cadmium, platinum, iron, nickel, magnetite, lead, lead alloy and lead dioxide.

6. The process according to claim 1, wherein the aqueous electrolyte comprises a buffer having a buffering range at a pH of from 7 to 11.

7. The process according to claim 1, wherein the aqueous electrolyte further comprises an anode corrosion inhibitor.

8. The process according to claim 1, wherein the aqueous electrolyte further comprises a complexing agent.

9. The process according to claim 1, wherein a molar ratio of α,β-unsaturated ester and carbonyl compound used is from 0.25 to 4.

10. The process according to claim 1, wherein the carbonyl compound is an aldehyde.

11. The process according to claim 1, further comprising subsequently transesterifying the γ-hydroxycarboxylic ester formed to the corresponding γ-lactone.

12. The process according to claim 1, further comprising subsequently transesterifying the γ-lactone formed to a γ-hydroxycarboxylic ester.

13. The process according to claim 1, further comprising subsequently hydrolyzing the γ-lactone, γ-hydroxycarboxylic ester, or both, to γ-hydroxycarboxylic acid.

* * * * *